US006809048B1

(12) United States Patent
Jacobs

(10) Patent No.: US 6,809,048 B1
(45) Date of Patent: Oct. 26, 2004

(54) BULKED FABRIC FILM LAMINATE

(75) Inventor: Rob L. Jacobs, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 442 days.

(21) Appl. No.: 09/141,859

(22) Filed: Aug. 28, 1998

Related U.S. Application Data

(62) Division of application No. 08/496,876, filed on Jun. 30, 1995, now Pat. No. 5,814,178.

(51) Int. Cl.$^7$ .............................................. B32B 31/00
(52) U.S. Cl. ..................... 442/401; 442/290; 442/351; 442/398; 428/141; 428/152; 428/196; 428/198; 428/315.9
(58) Field of Search ................................ 428/196, 198, 428/141, 152, 315.9; 442/290, 398, 401, 351

(56) References Cited

U.S. PATENT DOCUMENTS

| | | | |
|---|---|---|---|
| 2,626,883 A | 1/1953 | Boese ........................ 154/53.6 |
| 2,903,387 A | 9/1959 | Wade .......................... 154/101 |
| 3,043,733 A | 7/1962 | Harmon et al. ............. 156/209 |
| 3,169,899 A | 2/1965 | Steuber ........................ 161/72 |
| 3,380,868 A | 4/1968 | Moser ......................... 156/229 |
| 3,426,754 A | 2/1969 | Bierenbaum ................ 128/156 |
| 3,494,821 A | 2/1970 | Evans ......................... 161/169 |
| 3,632,733 A | 1/1972 | Yazawa .................... 264/342 R |
| 3,690,977 A | 9/1972 | Loft et al. ................... 156/167 |
| 3,692,618 A | 9/1972 | Dorschner et al. .......... 442/401 |
| 3,755,062 A * | 8/1973 | Schirmer ..................... 422/152 |
| 3,765,997 A | 10/1973 | Dunning ..................... 428/172 |
| 3,802,817 A | 4/1974 | Matsuki et al. ............... 425/66 |
| 3,949,128 A | 4/1976 | Ostermeier .................. 428/152 |
| 3,989,788 A | 11/1976 | Estes, Jr. et al. ............ 264/120 |
| 4,115,562 A | 9/1978 | Gragson et al. ............. 264/234 |
| 4,144,370 A | 3/1979 | Boulton ....................... 442/276 |
| 4,163,819 A | 8/1979 | Yung et al. ................. 428/198 |
| 4,164,600 A | 8/1979 | Yung et al. ................. 428/198 |
| 4,340,563 A | 7/1982 | Appel et al. ................. 264/518 |
| 4,342,812 A | 8/1982 | Selwood ..................... 442/381 |
| 4,352,849 A | 10/1982 | Mueller ....................... 428/213 |
| 4,379,192 A * | 4/1983 | Wahlquist et al. .......... 428/156 |
| 4,429,002 A | 1/1984 | Fukada et al. .............. 442/334 |
| 4,443,513 A | 4/1984 | Meitner et al. ............. 428/195 |
| 4,446,189 A | 5/1984 | Romanek .................... 428/152 |
| 4,725,473 A * | 2/1988 | Van Gompel et al. ...... 428/156 |
| 4,758,239 A | 7/1988 | Yeo et al. .................... 604/366 |
| 4,781,966 A | 11/1988 | Taylor ......................... 428/152 |
| 4,787,947 A | 11/1988 | Mays .......................... 156/160 |
| 4,842,930 A | 6/1989 | Schinkel et al. ............. 428/349 |
| 4,883,549 A | 11/1989 | Frost et al. .................. 156/161 |
| 4,999,232 A | 3/1991 | LeVan ......................... 428/113 |
| 5,143,779 A | 9/1992 | Newkirk et al. ............. 428/218 |
| 5,151,320 A | 9/1992 | Homonoff et al. .......... 442/384 |
| 5,152,946 A | 10/1992 | Gillette ....................... 264/230 |
| 5,232,533 A | 8/1993 | Tani et al. ................... 156/181 |
| 5,244,482 A | 9/1993 | Hassenboehler, Jr. et al. ........................ 55/528 |
| 5,296,289 A | 3/1994 | Collins ........................ 428/198 |
| 5,324,467 A | 6/1994 | Anderson, II ........... 264/173.15 |
| 5,368,927 A | 11/1994 | Lesca et al. ................. 442/398 |
| 5,376,198 A * | 12/1994 | Fahrenkrug et al. ........ 156/290 |
| 5,491,016 A * | 2/1996 | Kaiser et al. ................ 156/290 |
| 5,536,555 A * | 7/1996 | Zelazoski et al. ........... 428/138 |
| 5,595,567 A | 1/1997 | King et al. .................. 604/391 |
| 5,623,812 A * | 4/1997 | Todt .............................. 53/442 |
| 5,652,041 A * | 7/1997 | Buerger et al. ............. 156/290 |
| 5,712,008 A * | 1/1998 | Todt ............................ 156/290 |
| 5,814,178 A * | 9/1998 | Jacobs ......................... 156/290 |

FOREIGN PATENT DOCUMENTS

| | | | |
|---|---|---|---|
| DE | 2 063 961 | 7/1972 | ............ B29D/9/00 |
| DE | 2 307 681 | 8/1974 | |
| DE | 3 837 685 | 7/1989 | |
| EP | 0 556 749 | 8/1993 | ........... A61F/13/15 |
| GB | 2 271 315 | 4/1994 | ........... B32B/31/08 |
| JP | 49-047478 | 5/1974 | |
| JP | 54-015063 | 2/1979 | |
| JP | 59-178223 | 10/1984 | |
| JP | 61-268431 | 11/1986 | |
| JP | 6-2069874 | 8/1987 | |
| WO | 94 00292 | 1/1994 | ........... B32B/25/08 |
| WO | 96 11804 | 4/1996 | ........... B32B/27/12 |

OTHER PUBLICATIONS

Patent Abstracts of Japan, vol. 018, No. 243 (M–1602), May 10, 1994 & JP,A,06 031833 (Tonen Chem Corp), Feb. 8, 1994, See Abstract.

Patent Abstracts of Japan, vol. 95, No. 002 & JP,A07 040494 (Kao Corp), Feb. 10, 1995, See Abstract.

* cited by examiner

*Primary Examiner*—Terrel Morris
*Assistant Examiner*—John J. Guarriello
(74) *Attorney, Agent, or Firm*—William D. Herrick

(57) ABSTRACT

The present invention provides a process for producing a three dimensionally texturized liquid resistant laminate having a fibrous nonwoven layer and a liquid resistant layer. The process has the steps of placing the fibrous layer and the liquid resistant layer in juxtaposition to form a laminate, attaching the fibrous layer and the liquid resistant layer at a plurality of spaced-apart bond locations, heating the bonded laminate to a temperature that activates the latent shrinkability of the liquid resistant layer, and allowing the heated laminate to retract such that the liquid resistant layer shrinks and said fibrous layer forms gathers between said bond locations, thereby forming a three dimensional texture and heat annealing the laminate. The invention additionally provides a three dimensionally texturized laminate having a fibrous layer and a nonelastic liquid resistant layer. The layers of the laminate are joined at a multitude of spaced-apart bond sites, and the laminate is heat annealed, wherein the fibrous layer forms gathers between spaced-apart bond sites to provide the three dimensional texture and the laminate has a liquid resistant layer to fibrous layer length ratio between about 0.7 and about 0.95.

15 Claims, 2 Drawing Sheets

BULKED FABRIC FILM LAMINATE

This application is a divisional of application Ser. No. 08/496,876 entitled "Bulked Fabric Film Laminate" and filed in the U.S. Patent and Trademark Office on Jun. 30, 1995. now U.S. Pat. No. 5,814,178. The entirety of this application is hereby incorporated by reference.

BACKGROUND OF THE INVENTION

The present invention is related to a laminate containing a fibrous layer and a film layer. More particularly, the present invention is related to a liquid barrier laminate that is bulked and dimensionally stabilized.

Various disposable articles, e.g., diapers, training pants, protective garments, drapes, and feminine and incontinence care products, that contain an outer layer of a liquid impervious or barrier material are widely available. The outer layer of these articles is typically produced from a thermoplastic film. Although a film layer may provide the needed liquid barrier property, the film layer does not tend to provide desirable textural and visual properties.

One commercially useful approach in solving the textural and visual disadvantages is imparting a cloth-like texture on the outside of the film layer. For example, the desired texture can be imparted by laminating a nonwoven fabric adhesively or thermally on a film layer. U.S. Pat. No. 4,725,473 to Van Gompel et al. discloses, for example, a liquid impervious composite that is produced by depositing an unbonded nonwoven layer onto a film layer and then thermally bonding the composite. Alternatively, a bonded nonwoven fabric can be placed in juxtaposition with a film and then bonded to form a composite. These composites having soft, cloth-like textural properties are highly useful outer cover materials for various garments, such as diapers, training pants, incontinent garments and the like, although the textural properties of these composites may not be as pleasing as some natural fiber fabrics.

Additionally, although these composites are suitable for various uses, the composite may not be thermally stable since the layers, especially the film layer, tend to shrink and deform when exposed to a temperature above the softening temperature of the polymer or polymers forming the composite. It has been proposed that the film layer should be thermally annealed, to ameliorate the shrinkage problem, and then formed into the composite. Even though this annealing process provides a thermally stabilized composite, the texture and hand of the composite can be further improved.

There remains a need for further improving tactile properties and thermal stability of liquid resistant composites.

SUMMARY OF THE INVENTION

The present invention provides a process for producing a three dimensionally texturized liquid resistant laminate having a fibrous nonwoven layer and a liquid resistant layer, wherein the liquid resistant layer has a higher latent shrinkability than the nonwoven layer. The process has the steps of placing the fibrous layer and the liquid resistant layer in juxtaposition to form a laminate, attaching the fibrous layer and the liquid resistant layer at a plurality of spaced-apart bond locations, heating the bonded laminate to a temperature that activates the latent shrinkability of the liquid resistant layer, and allowing the heated laminate to retract such that the liquid resistant layer shrinks and said fibrous layer forms gathers between said bond locations, thereby forming a three dimensional texture and heat annealing the laminate.

The invention additionally provides a three dimensionally texturized laminate having a fibrous layer and nonelastic liquid resistant layer. The layers of the laminate are joined at a multitude of spaced-apart bond sites, and the laminate is heat annealed, wherein the fibrous layer forms gathers between spaced-apart bond sites to provide the three dimensional texture and the laminate has a liquid resistant layer to fibrous layer length ratio between about 0.7 and about 0.95.

The term "nonelastic" as used herein refers to any polymeric material which, upon application of a stretching force, is not recoverably stretchable to a stretched, biased length which is more than 125% of its original unbiased length, and the term "recoverable" refers to a contraction of more than 40% of its stretched length upon release of the stretching force. The term "spunbond fiber nonwoven web" refers to a nonwoven fiber web of small diameter filaments that are formed by extruding a molten thermoplastic polymer as filaments from a plurality of capillaries of a spinneret.

The extruded filaments are cooled while being drawn by an eductive or other well-known drawing mechanism. The drawn filaments are deposited or laid onto a forming surface in a generally random, isotropic manner to form a loosely entangled fiber web, and then the laid fiber web is subjected to a bonding process to impart physical integrity and dimensional stability. The production of spunbond webs is disclosed, for example, in U.S. Pat. No. 4,340,563 to Appel et al., U.S. Pat. No. 3,802,817 to Matsuki et al. and U.S. Pat. No. 3,692,618 to Dorschner et al. Typically, spunbond fibers have an average diameter in excess of 10 $\mu$m and up to about 55 $\mu$m or higher, although finer spunbond fibers can be produced. The term "staple fibers" refers to discontinuous fibers, which typically have an average diameter similar to or somewhat smaller than that of spunbond fibers. Staple fibers are 30 produced with a conventional fiber spinning process and then cut to a staple length, from about 1 inch to about 8 inches. Such staple fibers are subsequently carded or air-laid and thermally bonded to form a nonwoven web. The term "meltblown fiber web" or "melt-spray fiber web" indicates a fiber web formed by extruding a molten thermoplastic polymer through a spinneret containing a plurality of fine, usually circular, die capillaries as molten filaments or fibers into a high velocity gas stream which attenuates or draws the filaments of molten thermoplastic polymer to reduce their diameter. In general, meltblown fibers have an average fiber diameter of up to about 10 $\mu$m, although thicker meltblown fibers can be produced. After the fibers are formed, they are carried by the high velocity gas stream and are deposited on a forming surface to form an autogenously bonded web of randomly dispersed, highly entangled meltblown microfibers. Such a process is disclosed, for example, in U.S. Pat. No. 3,849,241 to Butin. The term "flashspun fiber web" indicates a nonwoven fabric formed by spraying a high temperature, pressurized solution of fiber-forming polymer and a volatile solvent into a low-temperature and pressure environment to rapidly evaporate the solvent. Such process provides autogenously bonded microfiber nonwoven webs and is, for example, disclosed in U.S. Pat. No. 3,169,899 to Steuber. The term "hydroentangled fiber web" indicates a nonwoven fabric of continuous or staple fibers that are consolidated and entangled by streams of liquid jet. Hydroentangled nonwoven fabrics of staple length fibers and continuous filaments are disclosed, for example, in U.S. Pat. No. 3,494,821 to Evans and U.S. Pat. No. 4,144,370 to Bouolton.

DETAILED DESCRIPTION OF THE INVENTION

Figure 1:
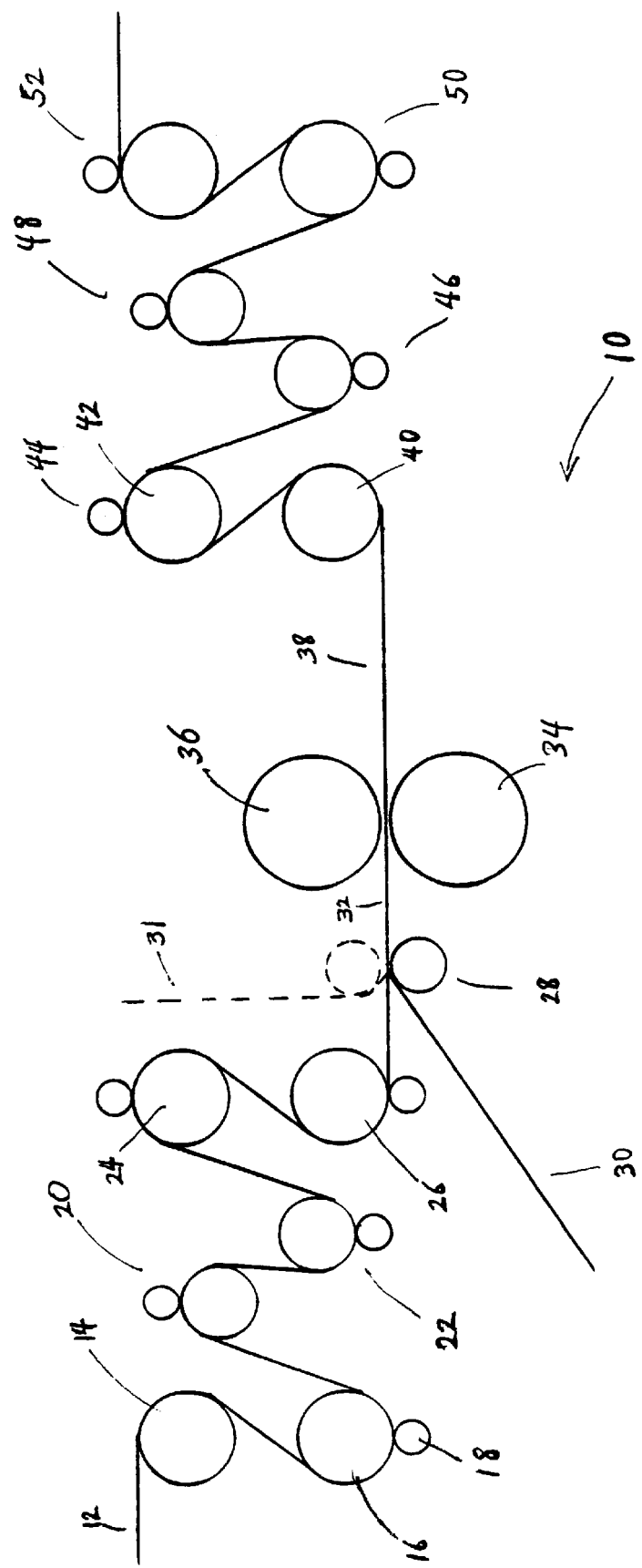
FIG. 1 illustrates an exemplary process for producing the three dimensionally texturized laminate of the invention.

The present invention provides a three dimensionally texturized liquid resistant laminate containing at least one fibrous layer and at least one liquid resistant layer. In accordance with the present invention, the fibrous layer and the liquid resistant layer are placed in juxtaposition and bonded to impart spaced-apart bond sites, forming a unitary laminate, and then the laminate is thermally annealed to shrink the liquid resistant layer, texturizing and heat stabilizing the laminate. The laminate provides highly desirable properties including improved loft, softness, cloth-like texture and pleasing gathered appearance. In addition, the laminate is heat stabilized and is dimensionally stable such that the laminate can be used even in various applications in which the laminate is exposed to a relatively high temperature, such as steam sterilization. More specifically, the three dimensionally texturized laminate in general is thermally stable up to the annealing temperature of its production process.

The fibrous layer of the laminate is selected from various nonwoven fabrics including spunbond fiber webs, meltblown fiber webs, hydroentangled fiber webs and laminates thereof. Additionally suitable materials for the fibrous layer include woven fabrics and knits. Of these, more particularly desirable are spunbond fiber webs for their desirable strength, textural properties and cost. Although the thickness and weight of the fibrous layer may vary widely, a fibrous web suitable for the fibrous layer desirably has a basis weight between about 0.1 osy (3 g/m$^2$) and about 3 osy (102 g/m$^2$), desirably between about 0.3 osy (10 g/m$^2$) and about 1.5 osy (50 g/m ), more desirably between about 0.4 osy (13 g/m$^2$) and about 1.2 osy (40 g/m$^2$).

The liquid resistant layer of the laminate is selected from thermoplastic films and thermoplastic microfiber nonwoven webs, more particularly nonelastic films and microfiber nonwoven webs, and the layer may be breathable or non-breathable, as further discussed below. Desirably, the liquid resistant layer has a hydrostatic head of at least about 20 centimeters (cm) as determined in accordance with the standard hydrostatic pressure test AATCCTM No. 127-1977.

The thickness and weight of the liquid resistant layer may also vary widely. However, a more desirable liquid resistant layer for the invention has a thickness between about 0.3 mil (7 μm) and about 1 mil (25 μm) or even thicker for films and between about 1 mil (25 μm) and about 10 mil (250 μm) for meltblown webs.

In accordance with the present invention, the liquid resistant layer exhibits a higher level of latent shrinkability than the fibrous layer. In general, latent shrinkability is imparted in a thermoplastic material when the material is stretched to thin or to orient the polymer molecules of the material. Typically, a thin thermoplastic material (e.g., film or microfiber web) is drawn or oriented to improve strength properties of the material in the oriented direction. In addition to improving strength properties, an orienting or stretching process can be used to reduce the thickness of or to down gauge the liquid resistant layer material such that an improved vapor transmittability and a more economical use of the material can be achieved. As is known in the art, different levels of molecular orientation can be imparted in the liquid resistant layer by controlling the extent of stretching or drawing. In general, such improved gauge and improved strength properties of the thermoplastic material contain increased molecular stress and strain. When such oriented thermoplastic material is exposed to a temperature that is high enough to allow some degree of molecular movements, i.e., a temperature above the glass-transition temperature $T_g$, more particularly above the softening temperature, of the thermoplastic polymer, the molecules of the thermoplastic material rearrange to relieve the molecular stress and strain. As a result of the molecular movement, the thermoplastic material shrinks generally in the direction of the molecular orientation, in which the extent of shrinkage typically corresponds to the extent of molecular orientation imparted in the thermoplastic material. Consequently, different levels of molecular orientation can be imparted in the liquid resistant layer by controlling the extent of molecular orientation.

The laminate of a liquid resistant layer and a fibrous layer having a desirable level of differences in latent shrinkability can be produced, for example, in accordance with a process 10 illustrated in FIG. 1. A film 12 is fed through a series of heated rollers, e.g., 14 and 16, to uniformly heat the film 12 to a temperature (stretching temperature) between the glass-transition temperature $T_g$ and the melting point $T_m$ of the polymer forming the film, more desirably between the softening temperature and the melting point $T_m$ of the polymer forming the film. For example, when a ethylene polymer or propylene polymer liquid resistant layer is utilized, particularly desirable stretching temperatures for the liquid resistant layer are in the range between about 60° C. and about 120° C. As illustrated in FIG. 1, the last heated roller 16 is equipped with an accompanying stack roller 18 and the film is passed through the nip formed by the rollers 16 and 18 such that the speed of the film over the heated rollers can be controlled. The heated film 12 is then fed to the nip formed by a first speed adjustable stack roller set 20, and then the film is passed to the nip formed by a second speed adjustable stack roller set 22. The stack rollers are designed such that the speed of the film traveling through the stack rollers can be controlled by varying the rotational speed of the rollers. The peripheral linear speed of the first stack roller set 20 is controlled to be faster than the peripheral linear speed. of the heated rollers 14 and 16 so as to apply a stretching tension to stretch and orient the molecules of the film. The peripheral linear speed of the second stack roller set 22 is yet faster than the peripheral linear speed of the first stack roller set 20, sequentially further stretching and orienting the heated film 12. Although FIG. 1 illustrates the stretching process with only two stack roller sets, the number of stack roller sets can vary widely. In accordance with the invention, the liquid resistant layer can be stretched to any desired level. However, it is particularly useful to stretch the layer to a length in the range between about 200% and 600% of the original length.

The stretched film 12 is then cooled desirably to a temperature in which the movement of the oriented molecules of the film is largely prevented, e.g., below the softening temperature of the film, by passing it over chill rollers or chill stack rollers 24 and 26. The cooled film is passed over a guiding roll 28 where a fibrous web 30 is placed in juxtaposition with the film, forming a laminate structure 32. Optionally, as illustrated with dotted lines in FIG. 1, one or more additional layers 31 of fibrous webs and/or films can be added to the laminate structure 32.

The laminate structure 32 is then bonded using a bonding process that imparts a plurality of spaced-apart bond sites such that the layers of the laminate structure are attached to each other at the bond sites and are independently moveable at the regions between adjacent bond sites. Suitable bonding processes for the present invention include thermal pattern bonding processes and ultrasonic bonding processes and adhesive bonding processes. Of these, ore desirable are thermal pattern bonding processes, and more desirable thermal pattern bonding processes impart uniformly distributed bond sites throughout the laminate structure. Returning to FIG. 1, the laminate structure 32 is bonded by feeding it through the nip formed by abuttingly placed pattern bonding rolls. In general, a pattern bonding process applies heat and pressure to effect a multitude of bond sites at limited areas of the laminate structure by passing the laminate structure through the nip formed by a heated pattern bonding roll pair, e.g., a pattern roll 34 and an anvil roll 36. One or both of the roll pair have a pattern of spaced-apart raised regions on the surface, which effects the bond sites, and are heated to an appropriate temperature. Appropriate roll temperatures and nip pressures are generally influenced by parameters such as speed, basis weight and component polymers of the laminate. For example, a bonding process for a laminate of a polypropylene nonwoven fabric and a polypropylene film has a roll temperature between about 200° F. (93° C.) and about 350° F. (177° C.) and a nip pressure between about 200 pounds per linear inch (phi) (35 kg/cm) and about 1000 pli (175 kg/cm). A particularly desirable bond pattern imparts evenly distributed bond sites throughout the laminate and imparts a total bonded area between about 5% and about 40%, desirably between about 8% and about 20%, based on the total planar surface area of the laminate, and the, pattern imparts between about 50 and 500 bond sites per square inch.

The bonded laminate 38 is then thermally annealed to heat stabilize and to shrink the film layer. The laminate 38 is passed over a series of heated rollers, e.g., 40 and 42, to uniformly heat the laminate 38 to a temperature (annealing temperature) equal to or higher than the above-mentioned stretching temperature but below the melting point $T_m$ of the polymer that forms the lowest melting layer of the laminate. According to the present invention, it is highly desirable to heat the laminate to an annealing temperature that is higher than the above-discussed stretching temperature. More particularly, a suitable range for the annealing temperature is between about 5° C. and about 30° C. higher than the stretching temperature, provided that the annealing temperature is lower than the melting point of the lowest melting layer of the laminate. As mentioned above, the thermal stability of the annealed laminate is essentially stable up to the annealing temperature. Consequently, it is highly advantageous to anneal the laminate at a higher temperature, provided that the temperature is not so high as to melt the lowest melting component layer of the laminate.

Returning to FIG. 1, the last heated roller 42 is equipped with an accompanying stack roller 44, and the laminate 38 is passed through the nip formed by the stack rollers 42 and 44 such that the speed of the laminate 38 over the heated rollers can be maintained at a controlled speed. The heated laminate is then fed to the nip formed by a third variable speed stack roller set 46, and then the laminate is passed to the nip formed by a forth variable speed stack roller set 48 while the elevated temperature of the laminate is substantially maintained. The third stack roller set 46 is designed such that the speed of the heated laminate traveling through that the stack roller set is slower than the speed of the laminate over the heated rollers 40 and 42. While traveling through the third stack roller set 46, the heated film layer of the laminate shrinks and thermally anneals, relieving its molecular stress and strain stored therein. The peripheral linear speed of the forth stack roller set 48 is yet slower than the peripheral linear speed of the third stack roller set 46, sequentially further shrinking and annealing the heated film layer. While shrinking and annealing the film layer, the present process also anneals the fibrous layer of the laminate, even though the fibrous layer does not and is not induced to shrink as much as the film layer. Although FIG. 1 illustrates a thermal annealing process having only two stack roller sets, the number of stack roller sets can vary widely, and although the extent of shrinkage or retraction of the liquid resistant layer may vary widely, a particularly desirable level of shrinkage is between about 5% and 30%, more particularly between about 10 and 20%, of the pre-annealed length of the laminate. During the annealing process, the shrinkage of the film layer causes the fibrous layer, which has a lower latent shrinkage than the film layer, to gather and bulk up between adjacent bond sites, forming a three dimensionally texturized laminate and improving textural properties of the laminate. It is important to note that the size of each bond site, the total number of the bond sites and the distance between adjacent bond sites affect the extent of the three dimensional texturization. For example, one of controlling factors for the extent of texturization, i.e., the level of bulking up, of the laminate is the distance between adjacent bond sites provided that the film layer has a sufficient level of molecular orientation to accommodate such shrinkage. The annealed laminate is then cooled to a temperature in which the movement of the molecules of the film is largely prevented, e.g., below the softening temperature of the film, by passing it over chilled rollers or chilled stack rollers 50 and 52. The resulting annealed laminate is three dimensionally texturized and thermally stable, and the laminate exhibits highly desirable textural and visual properties. Although FIG. 1 is illustrated with a film as the liquid resistant layer, a microfiber web can similarly be processed in place of the film to provide a texturized laminate of the present invention.

Figure 2:
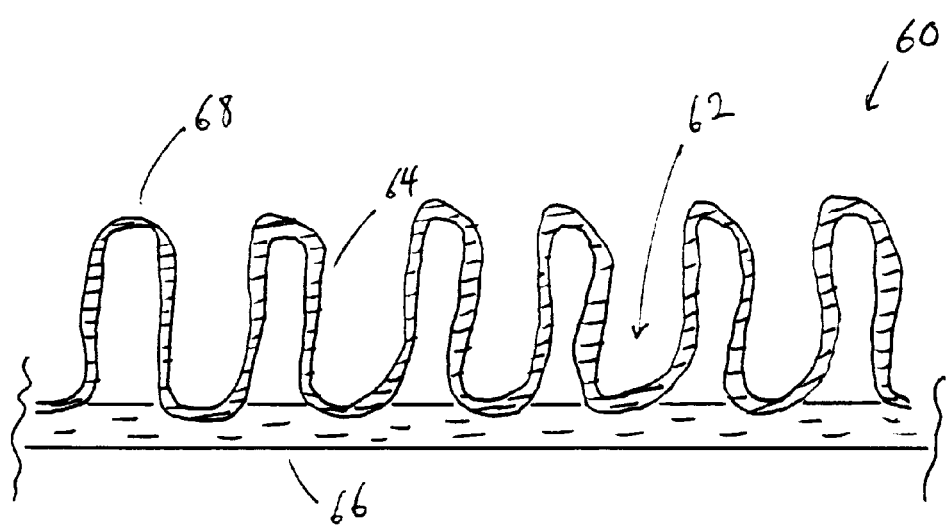
FIG. 2 illustrates a cross-sectional view of the three dimensionally texturized laminate.

Turning to FIG. 2, there is illustrated a cross-sectional view of the three dimensionally texturized laminate 60. FIG. 2 illustrates that the laminate 60 has a plurality of spaced-apart bond sites 62 that attach the fibrous layer 64 and the liquid resistant layer 66. As shown in FIG. 2, the fibrous layer 64 of the texturized laminate 60 is gathered between the bond sites 62, and these loop-like gathers that impart the three dimensional texture in the laminate are illustrated at 68.

The present laminate production process is not limited to the above-illustrated machine direction (MD) stretching and MD relaxing process. The liquid resistant layer can be stretched and the laminate can be relaxed in cross-machine direction (CD) using, for example, a tenter frame. Additionally, the laminate production process can be modified to apply biaxial, i.e., both CD and MD, stretching and relaxing steps to provide a highly and multidirectionally texturized laminate. In addition, the film layer can be separately stretched and then subsequently used to form the laminate. Alternatively, commercially available uniaxially or biaxially oriented films can be utilized, provided that the latent shrinkage of the films is higher than the latent shrinkage of the fibrous layer.

In accordance with the present invention, the texturized laminate can have widely different levels of texturization, from low to high texturization. Such variation in texturization can be accomplished by, for example, utilizing liquid resistant layers that have different levels of molecular orientation, applying different annealing temperatures and varying the duration of the annealing process. In general, a liquid resistant layer having a high level of molecular orientation provides a highly texturized laminate, and utilizing a high annealing temperature and/or extending the annealing duration also provides a highly texturized laminate. Additionally, as discussed above, the texturization level can be controlled by utilizing different bond patterns. The present annealing texturization process is highly advantageous in that the laminate can be texturized to a level that is highly difficult with prior art attempts. Particularly desirably texturized laminates of the invention have a ratio between a unit length of the liquid resistant layer and the length of the fibrous layer covering the liquid resistant layer (length ratio) of from about 0.7 to about 0.95, more desirably from about 0.8 to about 0.9, such that the laminates provide highly desirable textural properties as well as useful physical properties.

The liquid resistant layers suitable for the present invention are produced from thermoplastic polymers. More specifically, suitable films can be produced from thermoplastic polymers such as polyolefins, polyamides, polyesters, acrylic polymers, polyvinyl chloride, polyvinyl acetate, and copolymers and blends thereof. Suitable polyolefins include, for example, polyethylene, e.g., high density polyethylene, medium density polyethylene, low density polyethylene and linear low density polyethylene; polypropylene, e.g., isotactic polypropylene, syndiotactic polypropylene, blends thereof, and blends of isotactic polypropylene and atactic polypropylene; polybutylene, e.g., poly(1-butene) and poly(2-butene); polypentene, e.g., poly(1-pentene) and poly(2-pentene); poly(3-methyl-1-pentene); poly(4-methyl-1-pentene) and polybutadiene; and copolymers and blends thereof. Suitable copolymers include random and block copolymers prepared from two or more different unsaturated olefin monomers, such as ethylene/propylene copolymers, butene/propylene copolymers, ethylene vinyl acetate and ethylene vinyl alcohol. Additionally suitable olefin copolymers include heterophasic propylene polymers disclosed in U.S. Pat. No. 5,368,927 to Lesca et al., which patent is herein incorporated by reference. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include poly(ethylene terephthalate), poly (butylene terephthalate), poly(tetramethylene terephthalate), poly(cyclohexylene-1,4-dimethylene terephthalate), and isophthalate copolymers thereof, as well as blends thereof. Suitable acrylic polymers include ethylene methyl methacrylate and the like. Of these suitable polymers, the more desirable polymers are polyolefins, olefin copolymers and blends thereof since such polymers are widely available and have useful chemical and mechanical properties. The most desirable polymers for the film layer are various polyethylenes, various polypropylenes, and blends and copolymers thereof. Films containing a suitable polymer can be produced in accordance with conventional methods, such as casting and blowing processes.

Liquid resistant layer materials suitable for the present invention may be breathable, i.e., the liquid resistant layer has a water vapor transmission rate of at least 1000 grams per square meter for 24 hours as measured in accordance with ASTM E96-80, Method B. More desirably, the breathable liquid resistant layer material also exhibits microbe barrier properties. Typically, a breathable film contains evenly distributed micropores that are large enough to pass water vapor through the pores but small and tortuous enough to prevent liquid, and desirably also prevent microbes, from flowing therethrough. There are a number of ways to make a film breathable, which include microaperturing, solution leaching and the use of fillers. When fillers are used, a film is produced from a thermoplastic film composition that contains filler particles and then the film is stretched or crushed between rollers to crack the filler particles so as to create small gaps or apertures in the film. The term "filler" as used herein indicates particulates or other forms of materials that can be blended with a thermoplastic film composition and do not adversely interact with the film composition but can be uniformly dispersed in the film composition. In general, the fillers are in a particulate form and have an average particle size in the range of about 0.1 µm to about 10 µm. Exemplary suitable fillers include calcium carbonate, various kinds of clay, silica, alumina, barium sulfate, sodium carbonate, talc, calcium sulfate, titanium dioxide, zeolite, aluminum sulfate, diatomaceous earth, magnesium sulfate, magnesium carbonate, barium carbonate, kaolin, mica, carbon particles, calcium oxide, magnesium oxide, aluminum hydroxide and polysaccharide particulates, e.g., wood powder, pulp powders, chitin, chitosan and derivatives thereof. The filler material or a masterbatch of the filler material, typically, is dry blended with the thermoplastic resin pellets, e.g., in a tumble blender to uniformly disperse the filler, and then the physical mixture of the resin and the filler is processed to form a film. Again, a conventional film forming process, such as a casting or blowing process, can be used to form a film from the filled polymer composition.

As for the microfiber liquid resistant layer, suitable microfiber webs for the layer include meltblown fiber webs and flash spun fiber webs, and suitable microfiber webs can be produced from fiber-forming thermoplastics including polyolefins, polyamides, polyesters, acrylic polymers, polyvinyl chloride, polyvinyl acetate, and copolymers and blends thereof. Illustrative examples of the suitable thermoplastic polymers and blends thereof are disclosed above in conjunction with the film. Suitable processes for producing the microfiber layer include above-illustrated meltblown fiber web production processes and flash spun fiber web production processes.

The thermoplastic composition for the liquid resistant layer may additionally contain a bonding agent that facilitates improved bonding of the fibrous layer and the liquid resistant layer of the laminate, improving the bonding and peeling strength of the resultant laminate and lowering the temperature and pressure required to bond the laminate. The addition of the bonding agent is particularly important when the polymers of the fibrous layer and the liquid resistant layer are incompatible or not highly compatible. Examples of useful bonding agents include hydrogenated hydrocarbon resins such as Regalrez® series tackifiers, which are available from Hercules, Inc., and Arkon® series tackifiers, which are available from Arakawa Chemical (U.S.A.), Inc. Other suitable bonding agents include Zonatec® 501, which is produced by Arizona Chemical Co., and Eastman® 1023 PL resin, which is available from Eastman Chemical. Yet another group of suitable bonding agents includes ethylene copolymers such as ethylene vinyl acetate, ethylene ethyl acrylate, ethylene acrylic acid, ethylene methyl acrylate and ethylene butyl acrylate.

A suitable composition for the breathable film of the present invention may contain, based on the total dry weight of the composition, from about 10% to about 70% of a thermoplastic polymer and from about 30% to about 90% of a filler material. Optionally, the composition may additionally contain from about 2% to about 20% of a bonding agent. The liquid resistant layer composition may also contain processing aids, stabilizers, e.g., heat stabilizer, antistat, radiation stabilizer and light stabilizer, flame retardants, alcohol repellents, water repellents and the like.

Suitable materials for the fabric layer include nonwoven fabrics, e.g., spunbond webs, meltblown webs, hydroentangled webs, bonded staple fiber webs and the like; woven fabrics; knits and the like. Of these, particularly suitable materials for the fibrous layer are nonwoven fabrics produced from one or more of fiber-forming thermoplastic polymers. Suitable nonwoven fabrics for the present invention can be produced from any fiber-forming thermoplastic polymers including polyolefins, polyamides, polyesters, polyvinyl chloride, polyvinyl acetate and copolymers and blends thereof, as well as thermoplastic elastomers. Examples of specific polyolefins, polyamides, polyesters, polyvinyl chloride, and copolymers and blends thereof are illustrated above in conjunction with the polymers suitable for the film layer. Suitable thermoplastic elastomers for the fibrous layer include tri- and tetra-block styrenic block copolymers, polyamide and polyester based elastomers, and the like. In accordance with the invention, the polymer selected for the fibrous layer desirably has a melting point $T_m$ equal to or higher than the melting point $T_m$ of the polymer of the liquid barrier layer since it is not desirable to limit the annealing temperature of the annealing process to the melting point $T_m$ of the fibrous layer. The fibrous layer can be produced from monocomponent fibers, multicomponent conjugate fibers, or blends of more than one type of fibers. The fabric layer may also contain natural fibers, e.g., cotton fibers, wood pulp fibers and the like. Additionally suitable nonwoven fabrics are laminates of different nonwoven fabrics, e.g., spunbond webs, meltblown webs, hydroentangled web and bonded staple fiber webs. For example, U.S. Pat. No. 4,041,203 to Brock et al. teaches a laminate containing at least one spunbond web and one meltblown web, which is highly useful as the fibrous layer of the present invention. The patent in its entirety is herein incorporated by reference.

The three dimensionally texturized laminate of the present invention exhibits soft, drapable, lofty characteristics and has a considerably increased surface area when compared to the non-texturized laminate. Additionally, it has been found that the texturized laminate provides improved breathability when a breathable liquid resistant layer is utilized. The laminate is highly useful for various applications where, for example, cloth-like texture and liquid resistance are required. Illustrative examples of such applications include examining gowns, surgical gowns, industrial protective garments, surgical drapes, personal care article outer covers, diaper outer cover, training pants covers and the like. In addition, the laminate is thermally annealed such that it exhibits a high heat stability. The laminate is therefore highly suitable for various applications in which the laminate is exposed to a relatively high temperature, such as various sterilization procedures including steam sterilization and ethylene oxide sterilization processes. Consequently, the present laminate is an excellent material for sterilization packaging materials, e.g., sterile wraps, and disposable and sterilizable garments, e.g., surgical gowns. Typically, a sterilization package is used to sterilize and maintain instruments, such as surgical instruments for hospital operating rooms, in a sterilized condition until use. A large number of such instruments are currently packaged in sterile wraps. The most common method of packaging such instruments is called double, sequential wrapping wherein an instrument is rapped in a first piece of sterilization wrap with the loose ends being taped shut. Next, a second and separate sheet of sterilization wrap is used to wrap the instrument a second time. Once the second sheet of wrap has been wrapped around the instrument, the loose ends of the second sheet are taped closed and the wrapped instrument is sent through a sterilization process. After the wrapped instrument has been sterilized, it is normally placed in storage until actual use. As for disposable and sterilizable garments, there are many different types of disposable and sterilizable garments known in the art. Exemplary disposable and sterilizable garments are disclosed, for example, in U.S. Pat. No. 3,824,625 to Green and U.S Pat. No. 3,911,499 to Benevento et al., which patents are herein incorporated by reference. Many useful improvements, e.g., drapability, hand and heat stability, on such garments can be made by utilizing the present laminate.

The following examples are provided for illustration purposes and the invention is not limited thereto.

EXAMPLES

The following testing procedures were used.

Bulk: The bulk was measured using an Ames Thickness Tester, Model 3223. A3 inch (7.6 cm) diameter platen with total weight of 0.4 pounds (0.18 kg), including an attachment rod and weights, was placed on a 4 inch (10.2 cm) by 4 inch (10.2 cm) sample, and then the bulk was measured.

Drape Stiffness: This test determines the bending length and flexural rigidity of a fabric by measuring the extent of bending of the fabric under its own weight. The Drape Stiffness test was conducted in accordance with ASTM Standard Test D-1388, except the test specimen size was 1 inch×8 inch.

WVTR (Water Vapor Transmission Rate): This test determines breathability of a test specimen. The test was conducted in accordance with ASTM E96-80, Method B.

Example 1

A three dimensionally texturized, breathable film/spunbond nonwoven web laminate was prepared and tested for its properties.

A 1.5 mil (38 μm) blown film was prepared from a polymeric composition which contained, based on the total weight of the composition, about 18% of a heterophasic propylene polymer, about 12% of an ethylene-propylene random copolymer, about 5% of low density polyethylene and 65% of calcium carbonate. The composition additionally contained about 1.5 wt % of a pigment package. The heterophasic propylene polymer was Himont's KS051P (5 MFR) polypropylene based polymer; the random copolymer was Shell's RCP6D81; the low density polyethylene was Dow's LDPE 640; and the calcium carbonate was Supercoat™ which had a 1 μm average particle size and was obtained from ECCA Calcium Products, Inc., Alabama, a division of ECC International. The pigment package was Standard Color Corp.'s 11111 blue.

A 0.6 osy (20 g/m$^2$) spunbond nonwoven fabric was prepared from an ethylene-propylene random copolymer, Exxon's 9355, which was blended with 2 wt % of TiO$_2$ and 1 wt % of the 11111 blue pigment package. The spunbond fabric contained about 2.5 denier fibers and had a bond pattern that applied evenly distributed about 48 bond sites/cm$^2$ and had about 15% of the surface area covered by the bond sites.

The film was heated, stretched and cooled in the stretching section of the apparatus of the type that is illustrated in FIG. 1. The blown film was heated to about 190° F. (88° C.), stretched in the MD direction to about 340% of its original length and then maintained at about 170° F. (77° C.).

The stretched film was placed between two layers of the spunbond web in juxtaposition to form a laminate, and then the laminate was point bonded by feeding the web into the nip formed by a steel calender roll, which was heated to 270° F. (132° C.), and a steel anvil roll, which was heated to 240° F. (116° C.). The calender roll had about 10 points/cm$^2$ of raised bond points, and the total bond area occupied by the bond points was about 10% of the total surface area. The bonding rolls applied about 800 psi (56 kg/cm$^2$) pressure on the laminate. The bonded laminate had a caliper of about 24 mil (0.61 mm).

The bonded laminate was then annealed while allowing the film layer to shrink and the laminate to retract. The bonded laminate was heated by passing it over a series of heated roller to 230° C. at a speed of 360 feet/min (110 m/min). The heated laminate was fed through two sets of stack rollers that slowed the speed of the laminate to 300 feet/min (91 m/min), allowing the film layer to retract 15% in the machine direction, and then the laminate was cooled.

Comparative Example 1 (C1)

A non-texturized laminate containing a pre-heat annealed film layer was prepared and was tested for its properties.

A stretched film was produced in accordance with the procedure outlined in Example 1, and the film alone was then heat annealed in accordance with the procedure outlined for the bonded laminate in Example 1. The resulting film was placed between two layers of the spunbond fabric to form a laminate and then bonded in accordance with Example 1.

Example 2 (Ex2)

A heat annealed laminate was produced in accordance with Example 1, except a spunbond/melt blown/spunbond (SMS) composite fabric was used in place of the spunbond fabric.

A 0.6 osy (20 g/m$^2$) SMS composite was produced in accordance with U.S. Pat. No. 4,041,203 to Brock et al. The SMS composite contained two outer layers of a 0.225 osy (7.6 g/m$^2$) spunbond web, which was produced from the ethylene-propylene random copolymer composition disclosed in Example 1 for the spunbond fabric, and a 0.15 osy (5.1 g/m$^2$) middle meltblown fiber web layer, which was produced from Himont's high melt flow rate polypropylene, 3495G. The SMS composite was bonded with a pattern bond that applied about 48 bond sites/cm$^2$ and had about 15% of the surface area occupied by the bond sites.

Comparative Example 2 (C2)

Comparative Example 1 was repeated, except the SMS composite of Example 2 was used in place of the spunbond fabric.

Examples 1–2 and Comparative Examples 1–2 were tested for their properties, and the results are shown in Table 1.

TABLE 1

| Example | Bulk (mm) | Drape Stiffness (cm) | WVTR (g/m$^2$/24 hours) |
| --- | --- | --- | --- |
| Ex1 | 1.09 | 1.88 | 3860 |
| C1 | 0.61 | 3.17 | 3440 |
| Ex2 | 1.22 | 2.53 | 4490 |
| C2 | 0.41 | 3.30 | 3330 |

The bulk values of Ex1 and Ex2, compared to the bulk values of C1 and C2, demonstrate that the annealed laminates of the invention are three dimensionally texturized and have a highly improved bulk. In addition, the texturized laminates have lower drape stiffness values than corresponding comparative heat stabilized but non-texturized laminates (C1 and C2), indicating that the texturized laminates exhibit improved drapability and softness. The laminate also exhibited highly improved and desirable hand over the comparative laminates, and the breathability of laminate was surprisingly improved over the non-texturized laminates.

The three dimensionally texturized laminate of the invention provides highly improved textural properties and hand as well highly desirable dimensional stability against relatively high temperature exposures. The laminate is thus an excellent material for various applications, especially for liquid barrier applications, in which textural properties and/or heat stability is important. Moreover, the textural properties of the laminate make it particularly suitable for skin contacting uses, such as diapers, sanitary napkins, incontinence care products and various disposable garments.

What is claimed is:

1. A thermally stable, three dimensionally texturized liquid resistant laminate comprising a prebonded fibrous layer and a nonelastic liquid resistant layer having a higher latent shrinkability than said fibrous layer, said laminate having a three-dimensional texture and having been joined at a multitude of spaced-apart bond sites and heat annealed, wherein said fibrous layer forms gathers between spaced-apart bond sites.

2. The laminate of claim 1 wherein said laminate has a liquid resistant layer to fibrous layer length ratio between about 0.7 and about 0.95.

3. The laminate of claim 1 wherein said liquid resistant layer comprises a thermoplastic selected from polyolefins, polyamides, polyesters, acrylic polymers, polyvinyl chloride, polyvinyl acetate, and copolymers and blends thereof.

4. The laminate of claim 3 wherein said liquid resistant layer is selected from films and microfiber webs.

5. The laminate of claim 4 wherein said liquid resistant layer comprises a polyolefin.

6. The laminate of claims 5 wherein said liquid resistant layer comprises a heterophasic propylene polymer.

7. The laminate of claim 1 wherein said fibrous layer comprises a thermoplastic polymer selected from polyolefins, polyamides, polyesters, acrylic polymers, polyvinyl chloride, polyvinyl acetate, thermoplastic elastomers, copolymers and blends thereof.

8. The laminate of claim 1 wherein said fibrous layer has a basis weight between about 0.1 osy and about 4 osy.

9. The laminate of claim 8 wherein said fibrous layer is selected from a fabric selected from nonwoven webs, woven fabrics and knits.

10. The laminate of claim 9 wherein said fibrous layer is a spunbond fiber web.

11. The laminate of claim 9 wherein said laminate further comprises an additional fibrous layer.

12. The laminate of claim 1 wherein said laminate has been heat annealed at a temperature higher than the softening temperature of said liquid resistant layer and lower than the melting temperature of said liquid resistant layer and said fibrous layer.

13. A disposable article comprising the laminate of claim 1.

14. A sterilization packaging comprising the laminate of claim 1.

15. A garment comprising the laminate of claim 1.

* * * * *